United States Patent [19]
Arai et al.

[11] Patent Number: 5,255,026
[45] Date of Patent: Oct. 19, 1993

[54] STEREO EYE FUNDUS CAMERA

[75] Inventors: Akihiro Arai; Takeyuki Kato, both of Tokyo, Japan

[73] Assignee: Kabushiki Kaisha Topcon, Tokyo, Japan

[21] Appl. No.: 924,571

[22] Filed: Aug. 5, 1992

Related U.S. Application Data

[63] Continuation of Ser. No. 701,633, May 15, 1991, abandoned, which is a continuation of Ser. No. 472,385, Jan. 31, 1990, abandoned.

[30] Foreign Application Priority Data

Feb. 1, 1989 [JP] Japan ................. 1-23155

[51] Int. Cl.$^5$ ............................... A61B 3/14
[52] U.S. Cl. .................... 351/206; 351/211; 351/214; 354/62
[58] Field of Search ............ 351/206, 211, 214, 208, 351/240, 206, 207, 208; 354/62, 26

[56] References Cited

U.S. PATENT DOCUMENTS

| | | | |
|---|---|---|---|
| 4,068,932 | 1/1978 | Ohta et al. | 351/206 |
| 4,248,505 | 2/1981 | Muchel et al. | 351/206 |
| 4,396,260 | 8/1983 | Takizawa et al. | 351/206 |

Primary Examiner—Bruce Y. Arnold
Assistant Examiner—Hung X. Dang
Attorney, Agent, or Firm—Finnegan, Henderson, Farabow, Garrett & Dunner

[57] ABSTRACT

A stereo eye fundus camera has an illuminating optical system for illuminating the fundus of an eye to be tested through an objective lens, and a taking optical system for taking the eye fundus through the objective lens. The feature of the stereo eye fundus camera is that it has a mark projecting optical system for projecting at least three marks on the eye fundus such that the three marks are not on the same straight line.

6 Claims, 5 Drawing Sheets

STEREO EYE FUNDUS CAMERA

This application is a continuation of application Ser. No. 07/701,633, filed May 15, 1991, now abandoned, which is a continuation of Ser. No. 07/472,385, filed Jan. 31, 1990, now abandoned.

BACKGROUND OF THE INVENTION

1. Field of the Invention

This invention relates to a stereo eye fundus camera including an illuminating optical system for illuminating the fundus of an eye to be tested through an objective lens and a taking optical system for taking the eye fundus through the objective lens.

2. Prior Art of the Invention

Heretofore, a stereo eye fundus camera of the type shown in FIGS. 8 and 9 has been known. This conventional stereo eye fundus camera includes an objective lens 2 faced with an eye 1 to be tested, a taking system 3 for taking the fundus 1b of the eye 1, and an illuminating optical system 4 for illuminating the eye fundus 1b. The taking system 3 includes a beam splitting optical system for splitting beam passing through the objective lens 2 in order to see the object stereoscopically, a taking optical system 7 for taking the eye fundus, and an observing optical system k.

The beam splitting optical system 5 comprises a beam splitter 8 for splitting beam, a circular aperture diaphragm 9 having circular apertures (not shown) in symmetrical positions, and relay lenses 10a, 10b.

The taking optical system 7 comprises an image erecting poloprism 16a, 16b, etc. The numeral 17 denotes a taking lens. An observing optical system K comprises reflecting mirrors 11a, 11b, 12a, and 12b, an image erecting prisms 13a and 13b, field lenses 14a and 14b, eyepiece 15a and 15b, etc.

The illuminating optical system 4 comprises a perforated mirror V having an elongated opening (not shown), a condenser lens 18, a reflecting mirror 19, a relay lens 20, a shading plate 21 having a shading portion (not shown) formed on a central portion of its circular transparent plate, a half mirror 22, a condenser lens 23, an illuminating light source 24, a condenser lens 25, a taking light source 26, etc.

The beam emitted by an illuminating light source 24 passes through the condenser lens 23, the half mirror 22, the shading plate 21, the relay lens 20, the reflecting mirror 19, the condenser lens 18, the perforated mirror V and the objective lens 2 and illuminates the fundus 1b of the eye 1 to be tested. The shading plate 21 is conjugated with the pupil 1a of the eye 1 so that the image of the plate 21 is formed on the pupil 1a and the illuminating light is not made incident to the vicinity of the central portion of the pupil 1a.

The light reflected by the eye fundus 1b passes through the objective lens 2 and the elongated opening of the perforated mirror V and is then split into two portions by the beam splitting optical system 5. The split beam passes through the relay lenses 10a and 10b, the reflecting mirrors 11a, 11b, 12a and 12b, the image erecting prisms 13a and 13b, the field lenses 14a and 14b, and the eyepiece 15a and 15b and reaches observing eyes Q1 and Q2 by which the eye fundus 1b is stereoscopically observed.

When taking a photograph, the reflecting mirrors 11a and 11b are removed from the optical path and the taking light source 26 is lighted up. A pair of eye fundus images obtained when the eye fundus is viewed from both sides are taken in the taking film 17.

When the eye fundus is stereoscopically analyzed from the pair of eye fundus images, firstly, the common points to the pair of images are at least at three points plotted on two image screens so that the common points are not situated on the same straight line, and a mutual fixed position is occupied based thereon. Then, errors are found for each and every corresponding points on the image screens and the stereoscopic configurations of a papilla portion, etc. are analyzed.

However, in the above-mentioned stereo eye fundus camera, plotting of the fixed points must be manually performed by the operator and therefore the working is troublesome. There is also such a problem as that the correctly corresponding positions of the fixed points which are often at the crossing positions of the common blood vessels, brim of papilla, etc. to the two image screens are very difficult to find.

SUMMARY OF THE INVENTION

An object of the present invention is to provide a stereo eye fundus camera which is capable of taking a mark showing a common fixed point together with the fundus of an eye to be tested.

Another object of the present invention is to provide a stereo eye fundus camera which is capable of forming a well focused mark on the eye fundus whether the person to be tested (hereinafter simply referred to as the "patient") is hypermetropia or myopia.

The feature of the present invention is to provide a mark projecting optical system for projecting at least three marks on the eye fundus such that the three marks are not on the same straight line.

Another feature of the present invention is to provide a mark projecting optical system for forming projecting images of at least three marks in a conjugated position of the eye fundus between the objective lens and the taking optical system so that they are not on the same straight line.

Still another feature of the present invention is to provide a mark projecting optical system for projecting at least three marks on the eye fundus such that the three marks are not on the same straight line, the mark projecting optical system including a pin hole plate disposed in a position conjugated with the eye fundus and having at least three pin holes, and the pin hole plate being moved in such a manner as to be interlocked with the focusing lens.

DETAILED DESCRIPTION OF THE EMBODIMENT

The embodiment of the present invention will be described hereinafter with reference to the drawings.

Figure 1:
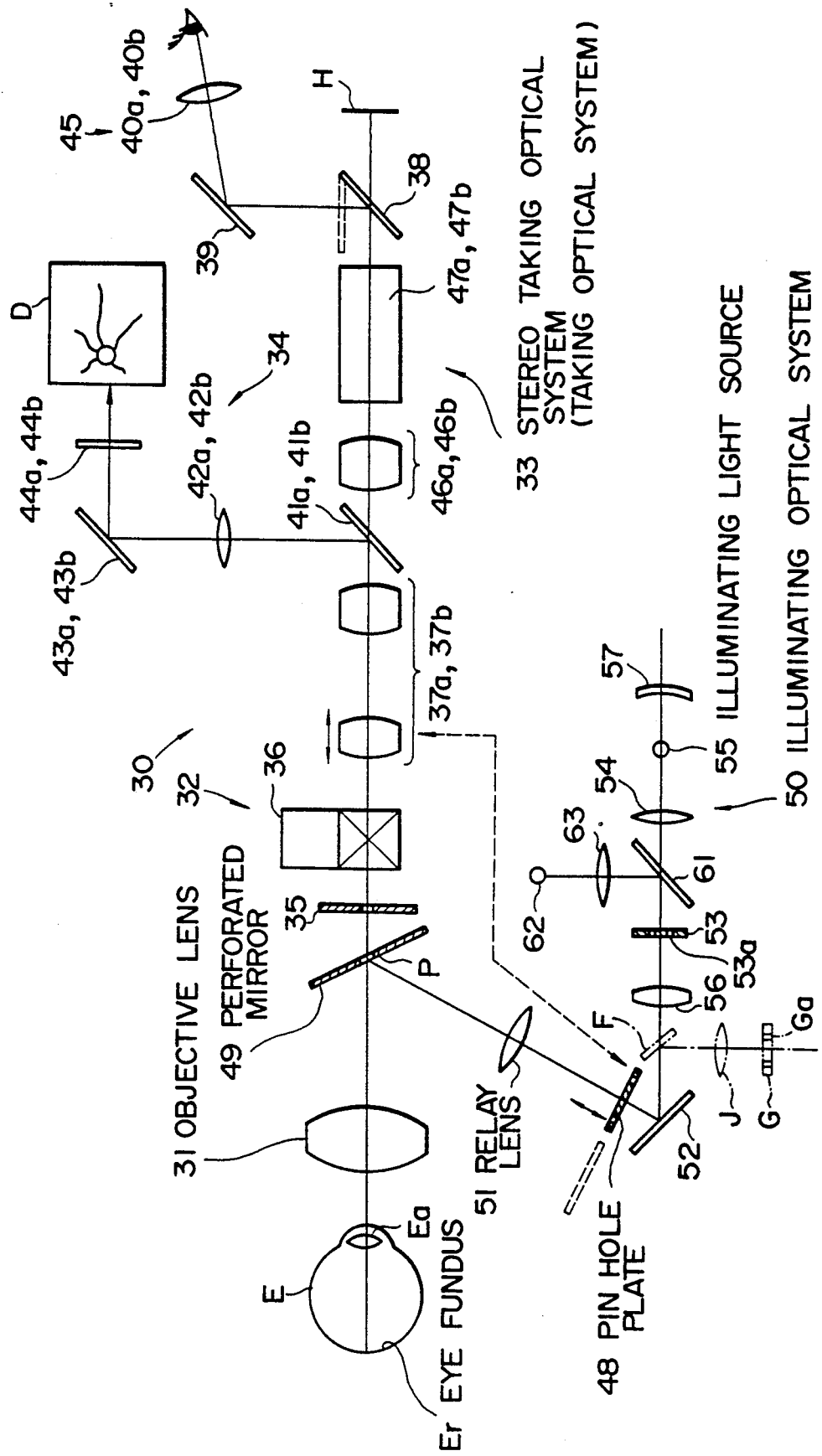
FIG. 1 is a side view showing the arrangement of an optical system of a stereo eye fundus camera according to the present invention.
Figure 2:
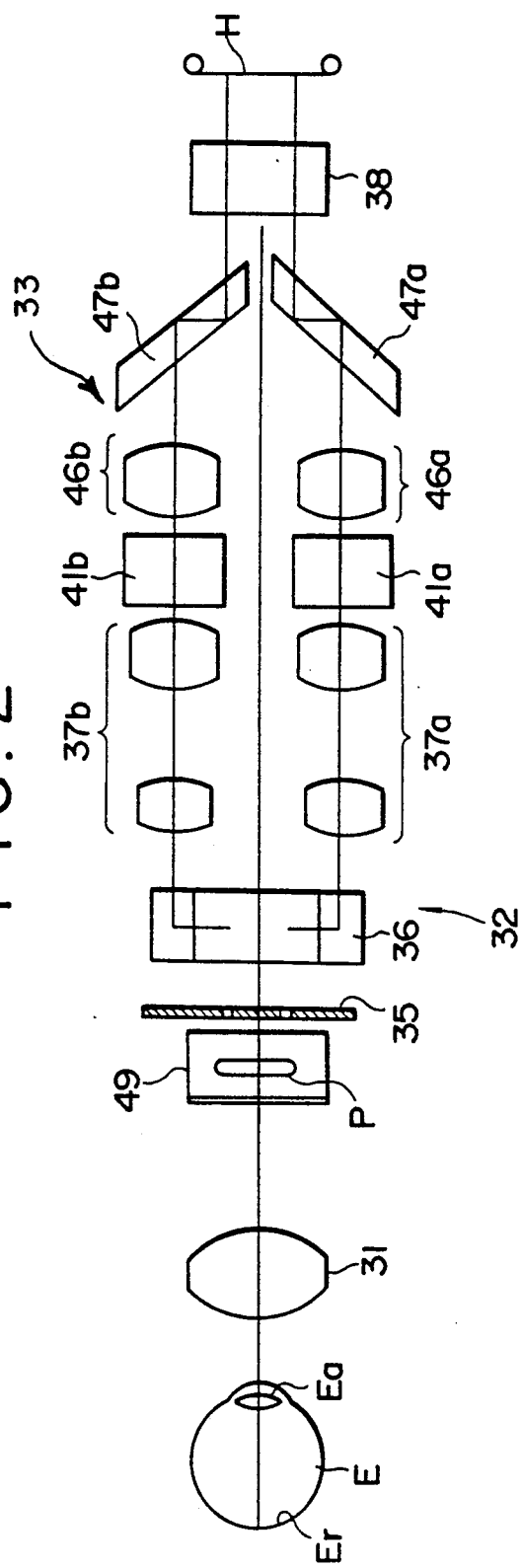
FIG. 2 is a plan view thereof.

FIG. 1 is a side view showing the arrangement of an optical system of a stereo eye fundus camera according to the present invention, and FIG. 2 is a plan view thereof. In the drawings, the numeral 30 denotes an observing system for observing the fundus Er of an eye E to be tested, and 50 is an illuminating optical system for illuminating the eye fundus Er.

The observing system 30 comprises an objective lens 31 facing the eye E, first and second photographing optical systems 32 and 33, a monitor optical system 34, and a stereo sighting optical system 45.

The first photographing optical system 32 comprises an aperture diaphragm plate 35 having two apertures (not shown), for splitting a beam passing through the objective lens 31 an image erecting poloprism 36, a focusing lenses 37a, a relay lens 46a and an image erecting poloprism 47a. The aperture diaphragm plate 35 is disposed in a position conjugated with a pupil Ea.

The second photographing optical system includes the aperture diaphragm plate 35, the image erecting poloprism 36, a focusing lens 37b, a relay lens 46b and an image erecting poloprism 47b. The reference character H denotes a taking film.

The stereo optical system 45 comprises reflecting mirrors 38 and 39, eyepiece 40a and 40b, etc. The reflecting mirror 38 is designed such that when taking, the mirror 38 moves upto a position shown by the broken lines and comes out of the optical path.

The monitor optical system 34 comprises half mirrors 41a and 41b, relay lenses 42a and 42b, reflecting mirrors 43a and 43b, and CCD 44a and 44b. The reference character D denotes a display for displaying the eye fundus image.

The illuminating optical system 50 comprises a perforated mirror 40 having an elongated opening P, a relay lens 51, a pin hole plate 48 disposed in a position conjugated with the eye fundus Er, a reflecting mirror 52, a relay lens 56, a ring aperture plate 53 having the transparent part in a ring 53a and disposed in a position conjugated with the pupil Ea, a condenser lens 54, and an illuminating light source 55. In order to take the eye fundus Er, the illuminating optical system 50 further comprises a half mirror 61, a lens 63, and a taking light source 62. The numeral 57 denotes a reflecting concave mirror 57.

The pin hole plate 48 is designed such that it can be moved to a position shown by the broken lines so as to be brought out of the optical path and moved in the direction as shown by the arrow in such a manner as to be interlocked with the focusing lens 37 in accordance with necessity. As a result of this movement, a spot image as will be described hereinafter is formed on the eye fundus in a well focused state whether the patient is myopia or hypermetropia.

Figure 3:
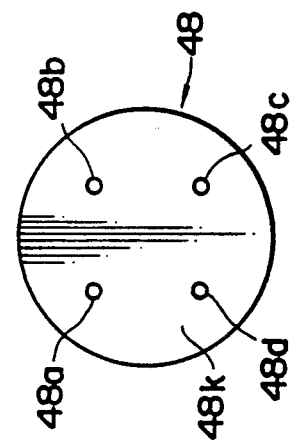
FIG. 3 is a plan view of a pin hole plate.

Also, the pin hole plate 48, as shown in FIG. 3, comprises a disk 48k having a transmittance of 30~50% and four pin holes (marks) 48a~48d having a transmittance of 100% and formed in the disk 48k.

The pin hole plate 48, the illuminating light source 55, the relay lens 51, the perforated mirror 49, etc. constitute the mark projecting optical system.

When the illuminating light source 55 is lighted up, the beam emitted by the illuminating light source 55 passes through the condenser lens 54, the half mirror 61, the ring aperture plate 53, the relay lens 56, the reflecting mirror 52, the pin hole plate 48, the relay lens 51, the perforated mirror 49 and the objective lens 31 and is then made incident to the eye E.

As the ring aperture plate 53 is disposed in a position conjugated with the pupil Ea, a ring aperture image (not shown) of the ring 53a is formed on the pupil Ea, and an illuminating light is made incident to the eye fundus Er from the ring aperture image.

Figure 4:
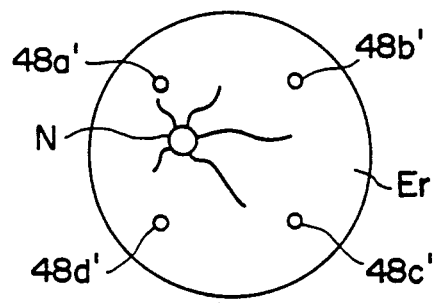
FIG. 4 is a schematic view of an eye fundus image.

On the other hand, as the pin hole plate 48 and the eye fundus Er are in conjugate relation and the beam from the illuminating light source 55 passes through the pin hole plate 48, spot images 48a'~48d' are formed on the eye fundus Er by the pin hole portions 48a~48d as shown in FIG. 4. The reference character N denotes a papilla.

The beam reflected by the eye fundus Er passes through the objective lens 31, the perforated mirror 49, the aperture diaphragm plate 35 and reaches the image erecting poloprism 36. Said reflected beam is split by the image erecting poloprism 36 and passes through the focusing lenses 37a and 37b, the half mirrors 41a and 41b, the relay lenses 42a and 42b, and the mirrors 43a and 43b and reaches the CCD 44a and 44b, and an eye fundus image is formed on the display D.

On the other hand, the beam passing through the half mirrors 41a and 41b passes through the relay lenses 46a and 46b, the image erected poloprisms 47a and 47b, and the mirrors 38 and 39 and then reaches the eyepiece 40a and 40b, and therefore the eye fundus Er can be stereoscopically observed.

When the eye fundus Er is taken, the taking light source 62 is lighted up and the reflecting mirror 38 is taken out of the optical path. The beam emitted by the taking light source 62 passes through the condenser lens 63, the half mirror 61, the ring hole plate 53, the relay lens 56, the reflecting mirror 52, the pin hole plate 48, the relay lens 51, the perforated mirror 49 and the objective lens 31 and is then made incident to the eye E. Therefore, the spot images 48a'~48d' are formed on the eye fundus Er in the same manner as described above.

Figure 5:
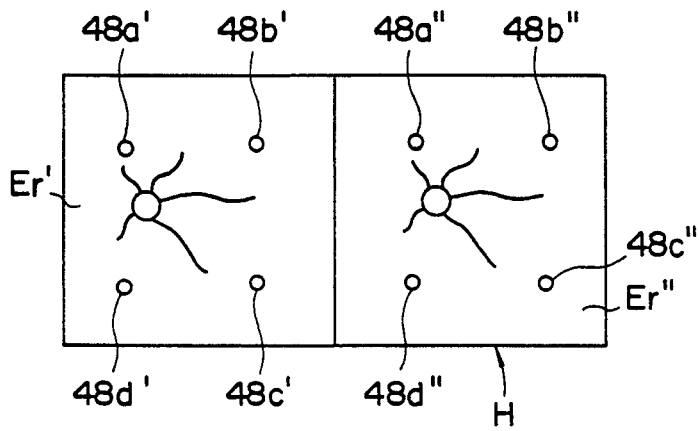
FIG. 5 is a schematic view of an eye fundus image formed on a taking film.

The beam reflected by the eye fundus Er, like the above, passes through the objective lens 31, the perforated mirror 49, the aperture diaphragm 35, the image erected poloprism 36, the focusing lenses 37a and 37b, the half mirrors 41a and 41b, the relay lenses 46a and 46b, and poloprisms 47a and 47b and reaches the taking film H. Therefore, the spot images 48a'~48d' and 48a''~48d'' are formed on the taking film H together with the eye fundus images Er' and Er'' as shown in FIG. 5.

As the spot images 48a'~48d' of this eye fundus image Er' and the spot images 48a''~48d'' of the eye fundus image Er'' show the same position of the eye fundus Er, it becomes the common fixed point for both of the eye fundus images Er' and Er''. Therefore, the common fixed points are not required to be plotted to the both images on the film H as in the prior art.

Although the pin hole plate 48 is disposed between the relay lens 51 and the mirror 52 in the above-mentioned embodiment, the present invention is not limited to this. For example, as is shown by the broken lines in FIG. 1, it may be designed such that a half mirror F is interposed between the mirror 52 and the relay lens 56 and a pin hole plate G is disposed in a position conjugated with the pin hole plate 48, and the light from the illuminating light source 55 is guided to the pin hole portion Ga of the pin hole plate G by optical fiber (not shown). The character J denotes a relay lens.

Figure 6:
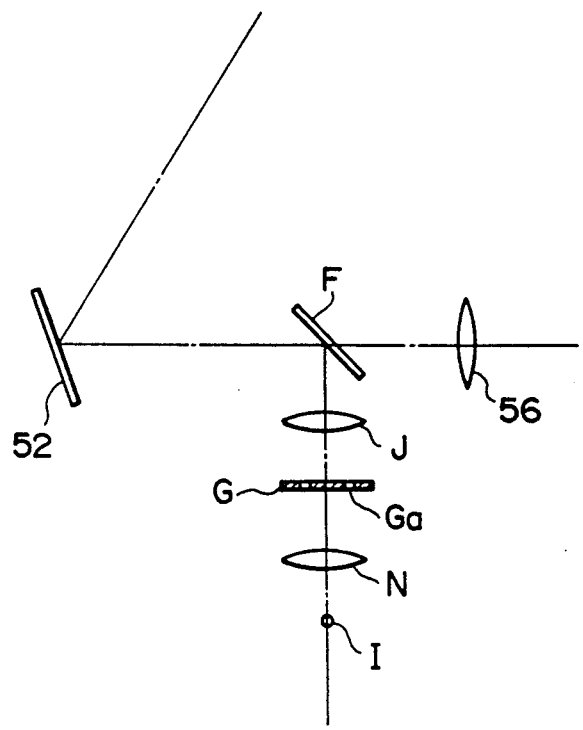
FIG. 6 is a schematic view of a second embodiment.

Also, as is shown in the second embodiment of FIG. 6, if a light source I and a condenser lens N are provided and the spread of the beam emitted by the pin hole Ga is made smaller than the illuminating beam (observing, taking beam), the depth of field of the spot image formed on the eye fundus Er becomes deep when compared with the whole illuminating light. In this case, for example, the pin hole plate G comprises a disk of a transmittance of 0%, and the pin hole portion Ga comprises by a hole of a transmittance of 100%.

Figure 7:
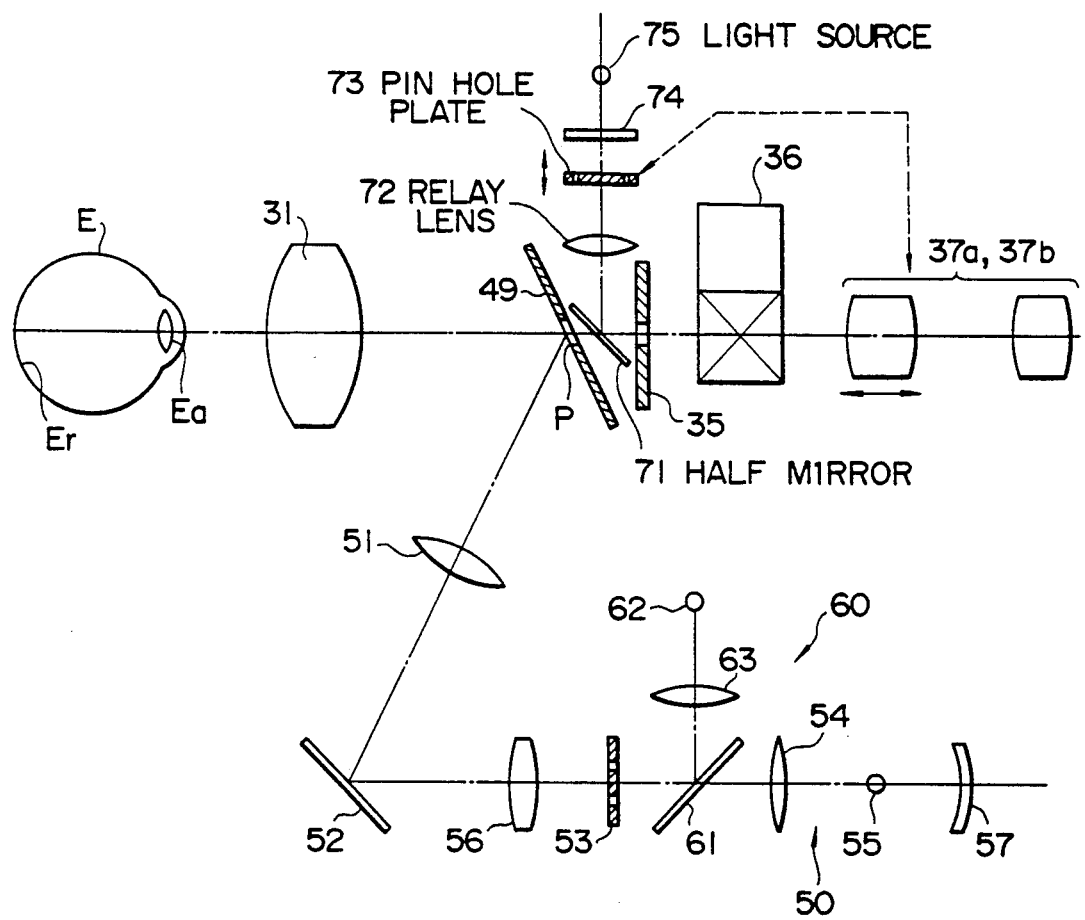
FIG. 7 is a schematic view of a third embodiment.
Figure 8:
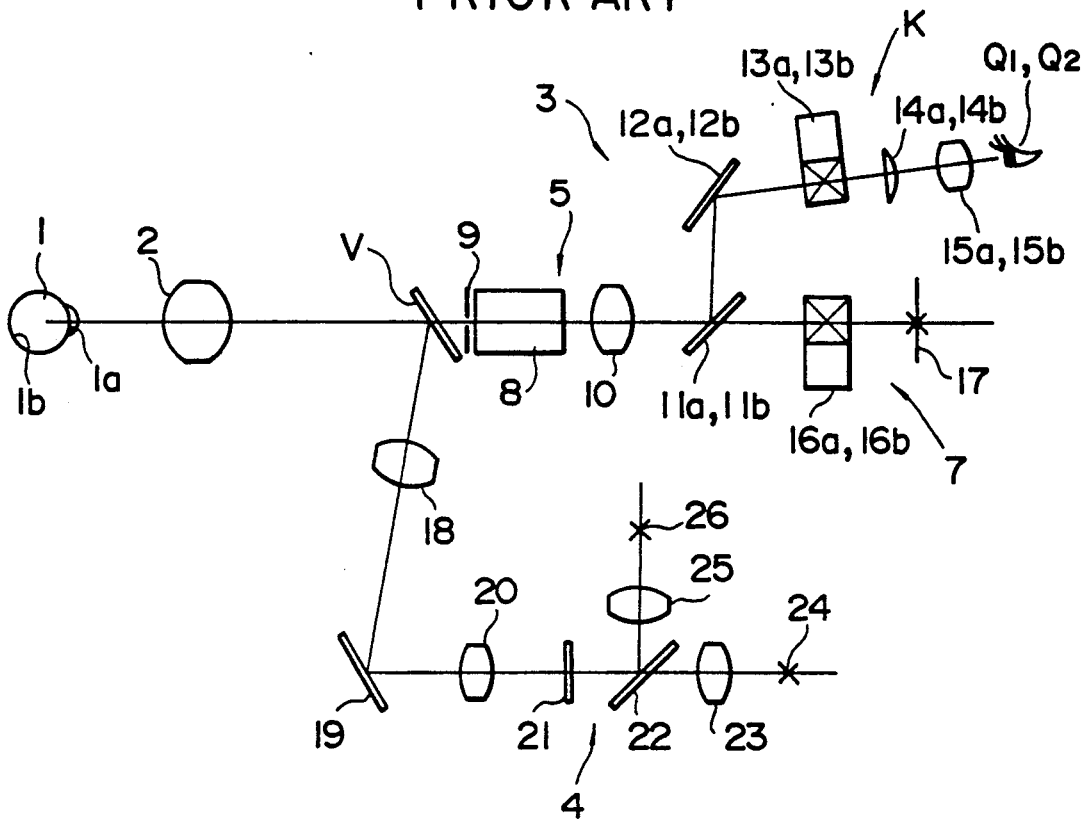
FIGS. 8 and 9 are schematic views showing the construction of the conventional stereo eye fundus camera.
Figure 9:
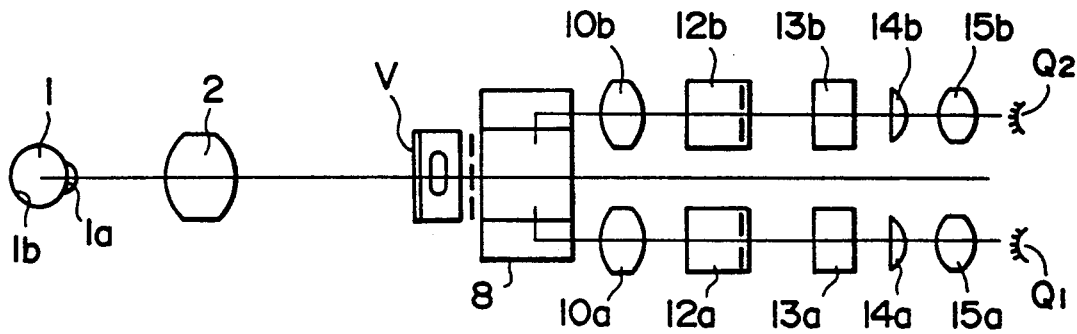

FIG. 7 shows the third embodiment, in which there is disposed a mark projecting optical system adapted to form a spot image in front of the splitting optical system 32 adapted to split the beam reflected by the eye fundus Er. By this mark projecting optical system, the spot image is formed on the GCD 44a and 44b and the taking film H.

In FIG. 7, the numeral 71 denotes a half mirror of a transmittance of, for example, about 90% or more and disposed between the perforated mirror 49 and the aperture diaphragm plate 35, the numeral 72 denotes a relay lens, the numeral 73 denotes a pin hole plate disposed in a position conjugated with the eye fundus Er, the numeral 74 denotes a diffusion plate, and the numeral 75 denotes a light source. In this embodiment, the image of the pin hole plate 73 is formed by the relay lens 72 in a position conjugated with the eye fundus image formed by the objective lens 31. And the half mirror 71, the relay lens 72, the pin hole plate 73, and the light source 75 constitute the mark projecting optical system.

The pin hole plate 73, like the above-mentioned embodiment, comprises a disk of a transmittance of 0% and four pin holes (see FIG. 3) of a transmittance of 100% and formed in the disk. This is, like the above-mentioned embodiment, moved in the direction as indicated by the arrow in such a manner as to be interlocked with the focusing lenses 37a and 37b and a pin hole image is always formed in a position conjugated with the eye fundus image.

In the above-mentioned embodiment, the spot image and a virtual image of the spot are formed on the eye fundus Er and in a position conjugated with the eye fundus Er. However, instead of the spot (white, red, blue, etc.), there may be formed a black point. The spot is not only a point but also may be various marks such as square, triangle, etc. And when the analysis is performed using the display D, a mark image may be formed on the eye fundus Er by infrared light instead of forming a spot on the eye fundus Er by a visible light.

Although four pin hole portions are formed in the pin hole plates 48 and 74 in the above-mentioned embodiment, the present invention is not limited to this. The pin hole portion may be four or more, or otherwise three. It is just the same as long as three points are not at least a linear line.

As described in the foregoing, according to the present invention, there is provided a mark projecting optical system for projecting at least three marks such that the three marks are not on the same straight line on the eye fundus, and there is also provided a mark projecting optical system for forming projecting images of at least three marks in a conjugated position of said eye fundus between the objective lens and the taking optical system so that they are not on the same straight line. Accordingly, mark and eye fundus images can both be photographed simultaneously in stereoscopic images with the mark means providing common fixed points of both stereoscopic images. Therefore, it is no longer required to plot the common points of both images of the eye fundus by hand as was done in the prior art. Therefore, the working efficiency of stereo analysis can be increased.

What is claimed is:

1. A stereoscopic eye fundus camera, comprising:
   illuminating optical means for applying a beam of light to the fundus of an eye which is to be tested through an objective lens;
   mark projecting optical means for projecting a mark onto said fundus; and
   stereoscopically photographing optical means, including first and second photographing optical systems, for simultaneously photographing, through said objective lens, said eye fundus and said mark which is projected onto the fundus by said mark projecting optical means.

2. The stereoscopic eye fundus camera according to claim 1, wherein said mark projecting optical means includes a movable spot diaphragm, and said first and second photographing optical systems each include a focusing lens for adjusting the focus thereof, said spot diaphragm being movable in accordance with adjustments of said focusing lens.

3. A stereoscopic eye fundus camera according to claim 2, wherein a diameter of a beam of light emitted from a spot of said spot diaphragm is predetermined to be smaller than that of a beam of illuminating light of said illuminating optical means at a point conjugate with the fundus.

4. A stereoscopic eye fundus camera, comprising:
   an illuminating optical system for applying a beam of light to the fundus of an eye which is to be tested through an objective lens;
   a mark projecting optical system for forming a mark image at a point conjugate with the fundus behind said objective lens; and
   a stereoscopically photographing optical system, including first and second photographing optical systems, for simultaneously photographing said mark image and the eye fundus through said first and second photographing optical systems.

5. The stereoscopic eye fundus camera according to claim 4, wherein said mark projecting optical system includes a movable spot diaphragm, and said first and second photographing optical systems each include a focusing lens for adjusting the focus thereof, said spot diaphragm being movable in accordance with adjustments of said focusing lens.

6. A stereoscopic eye fundus camera according to claim 5, wherein a diameter of a beam of light emitted from a spot of said spot diaphragm is predetermined to be smaller than that of a beam of illuminating light of said illuminating optical means at a point conjugate with the fundus.

* * * * *